(12) United States Patent
Castaldi et al.

(10) Patent No.: US 8,137,295 B2
(45) Date of Patent: Mar. 20, 2012

(54) MANUALLY POWERED PULSATING JET DEVICE

(76) Inventors: John Castaldi, Brooklyn, NY (US); Michael Sylvester Caramico, Brooklyn, NY (US)

( * ) Notice: Subject to any disclaimer, the term of this patent is extended or adjusted under 35 U.S.C. 154(b) by 1101 days.

(21) Appl. No.: 12/008,917

(22) Filed: Jan. 15, 2008

(65) Prior Publication Data

US 2009/0182250 A1    Jul. 16, 2009

(51) Int. Cl.
*A61H 7/00*    (2006.01)

(52) U.S. Cl. ........... 601/162; 601/161; 601/160; 433/80

(58) Field of Classification Search .......... 601/160–165; 433/80, 215, 229
See application file for complete search history.

(56) References Cited

U.S. PATENT DOCUMENTS

| | | | | |
|---|---|---|---|---|
| 3,703,170 A | * | 11/1972 | Ryckman, Jr. ................. | 601/162 |
| 5,033,961 A | * | 7/1991 | Kandler et al. ................. | 433/89 |
| 5,197,460 A | * | 3/1993 | Ito et al. ......................... | 601/162 |
| 5,303,868 A | * | 4/1994 | Kroll ............................. | 239/394 |
| 6,022,329 A | * | 2/2000 | Arnett et al. ................... | 601/155 |
| 6,375,459 B1 | * | 4/2002 | Kamen et al. ................... | 433/80 |
| 6,689,078 B1 | * | 2/2004 | Rehkemper et al. ........... | 601/162 |
| 7,080,980 B2 | * | 7/2006 | Klupt ............................. | 433/80 |
| 2004/0209222 A1 | * | 10/2004 | Snyder et al. ................... | 433/80 |
| 2004/0210186 A1 | * | 10/2004 | Arnett et al. .................... | 604/35 |

* cited by examiner

*Primary Examiner* — Justine Yu
*Assistant Examiner* — Si Lee
(74) *Attorney, Agent, or Firm* — Gertner Mandel & Peslak, LLC; Arthur M. Peslak

(57) ABSTRACT

A manually powered portable device for creating a high-pressure pulsating stream of water or other liquid is disclosed. The device is intended for use in flushing and cleaning dentures. The device has a reservoir for storing the water or liquid, a piston and cylinder for pressurizing the water, a trigger operated slide valve for releasing the water from the reservoir and a rotating cylinder for creating the pulsating flow through the output nozzle of the device.

1 Claim, 2 Drawing Sheets

MANUALLY POWERED PULSATING JET DEVICE

BACKGROUND OF THE INVENTION

The present invention relates to the field of devices for use in flushing and cleaning dentures. In particular, the present invention relates to a manually powered portable device for flushing dentures with a pulsating high-pressure stream of liquid. The small size and portability of the device make it particularly appropriate for travel as it can be easily packed in luggage or carry-on bags during air travel. Further, it is entirely self-contained and operates without batteries or other energy sources.

SUMMARY OF THE INVENTION

A manually powered pulsating liquid jet device for generating a pulsating flow of liquid for use in cleaning dentures comprising: a refillable liquid reservoir for holding liquid comprising a first inlet port through which the liquid enters the reservoir and a first outlet port; a one-way flow controller comprising a second inlet port and a second outlet port whereby the second inlet port is connected to the first outlet port to allow the liquid to exit but not to re-enter the reservoir therethrough; a piston with a handle external to the device and a mating cylinder connected to the second outlet port whereby withdrawing the piston from the cylinder will activate the one-way flow controller and cause liquid to be withdrawn from the reservoir; a spring loaded cord attached to the handle for pressurizing the liquid that is withdrawn from the reservoir; an outlet tube for the pressurized liquid comprising a first connection and a second connection whereby the first connection is fluidly connected to the second outlet port; a valve that can be moved from a first position to a second position for controlling flow of the pressurized liquid through the outlet tube; a rotating cylinder connected to the spring loaded cord comprising one or more central flow passages and a periphery with the openings on the ends of the central flow passages in the periphery adjacent to the second connection of the outlet tube; and an output nozzle adjacent to the rotating cylinder; whereby moving the valve from the first position to the second position allows the pressurized liquid to flow through the second connection of the outlet valve, into, and through the central flow passage and out of the output nozzle on a pulsating basis.

DETAILED DESCRIPTION OF THE INVENTION

Figure 1:
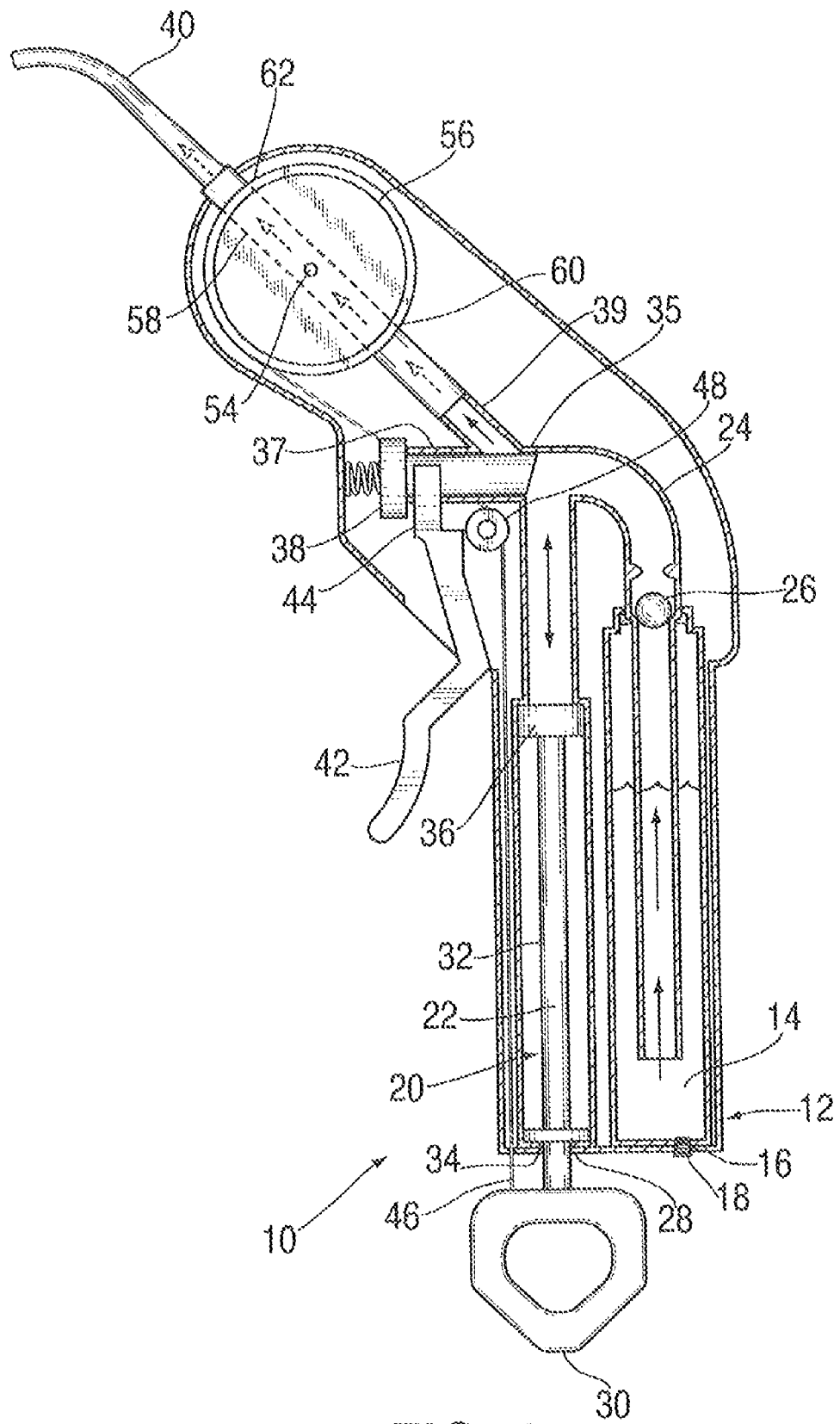
FIG. 1 is a cross-sectional view of an embodiment of the present invention.

The present invention will now be described in connection with the presently preferred embodiment thereof as illustrated in the drawings. Those of ordinary skill in the art will recognize that many obvious modifications may be made thereto without departing from the spirit and scope of the present invention.

The pulsating jet device 10 of the present invention is illustrated in FIG. 1. The device 10 comprises a generally cylindrical distal end 12. The distal end 12 comprises a fluid reservoir 14 that is manually filled with liquid through opening 16 at the bottom thereof. The opening 16 is fitted with a removable plug or cap 18. The distal end 12 further comprises a cylinder 20 and piston 22. The piston 22 is adapted to slide within the cylinder 20.

A tube 24 fluidly interconnects the piston 22 and reservoir 14. The tube 24 is fitted with a ball type check valve 26 that will allow fluid in the reservoir 14 to pass out through tube 24 but not re-enter the reservoir.

The piston 22 is fitted into the cylinder 20 through opening seal 28. The piston 22 comprises a handle 30 that extends outside the distal end 12 of the device 10. The piston 22 further comprises a shaft 32 and fixed bushings 34 and 36. The bushings 34 and 36 allow the piston 22 to slide in the cylinder 20 but prevent fluid from the reservoir 14 from leaking behind the end caps 34.

The tube 24 further comprises a y-type connection 35. One arm 37 of the Y-type connection 35 is fitted with a spring-loaded slide valve 38. As explained further below, depending upon the position of the slide valve, the other arm 39 will be fluidly interconnected with the external nozzle 40.

The device 10 further comprises an external trigger 42. The trigger 42 engages the slide valve 38 by means of collar 44. As explained further below, the trigger 42 is used to activate the slide valve 38.

Figure 2:
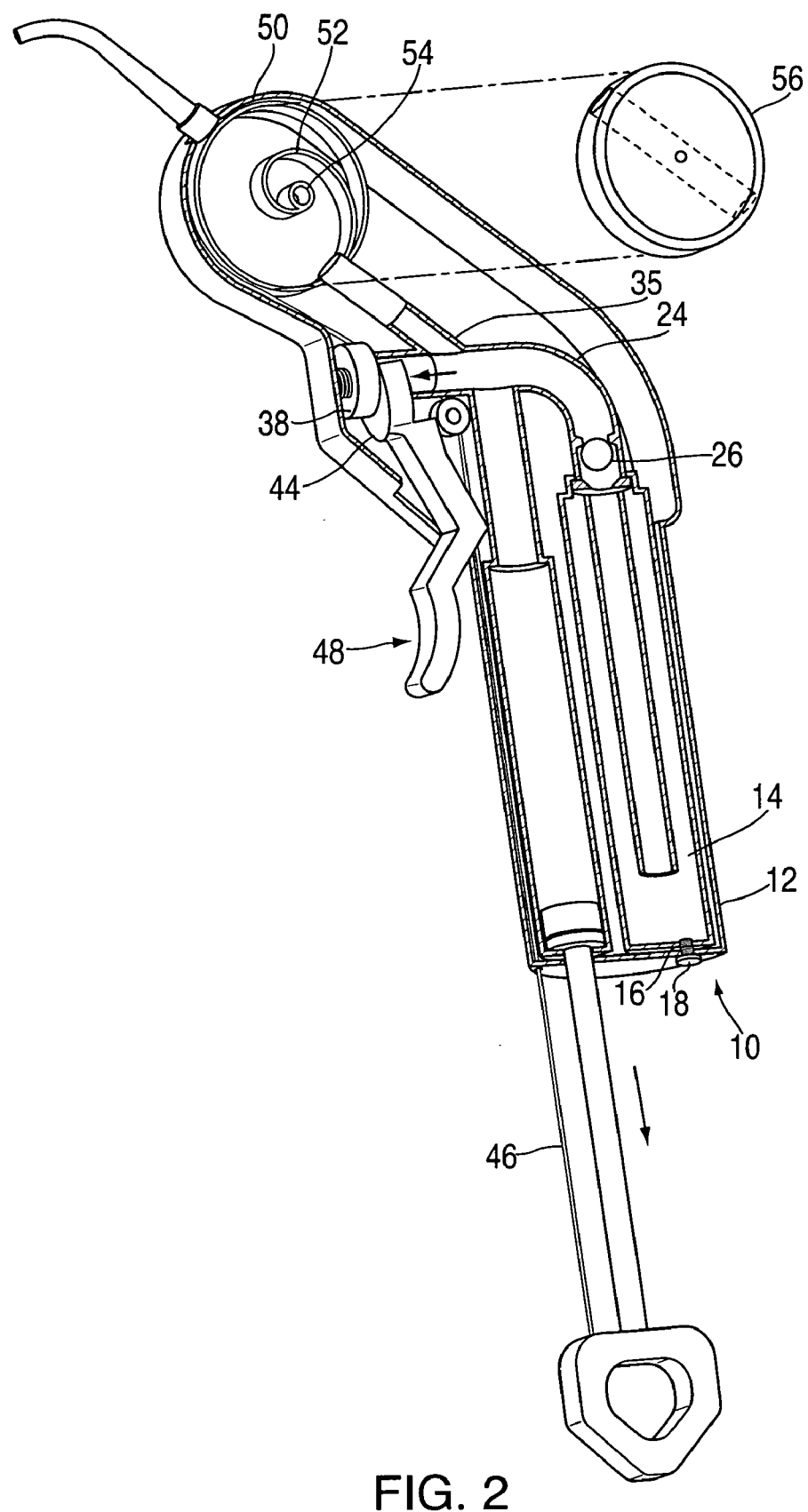
FIG. 2 is a cross-sectional view of the embodiment of FIG. 1 illustrating the operation of the present invention.

As illustrated in FIG. 2, the handle 30 is fitted with a cord 46. The cord 46 is wound around a spool 48 and then connected to the outside of a spring cylinder 50. The spring cylinder 50 comprises an internal leaf spring 52.

The spring cylinder 50 is rotated about an axle 54. A pulse generating cylinder 56 is connected to the same axle 54 so that the spring cylinder 50 and the pulse generating cylinder will rotate in tandem as the cord 46 is extended from the distal end 12.

The pulse generating cylinder 56 contains a central tubular path 58. The tubular path 58 is open to the exterior of the pulse generating cylinder 56 on each end 60 and 62.

The operation of the pulsating jet device 10 will now be described in detail. Initially, the fluid reservoir 14 will be filled with liquid through opening 16. Next, the user will withdraw the piston 22 by pulling on the handle 30. The cord 46 which is connected to the handle 30 will also be withdrawn by the handle 30. By withdrawing the piston 22, the check valve 26 will open and fluid will be withdrawn from the reservoir 14 into cylinder 20. The tension in the cord 46 will pressurize the liquid in the cylinder 20. The user will then squeeze the trigger 42 which will cause the slide valve 38 to move laterally against the spring 37. When the slide valve 38 is moved, the area 39 of the y-connection 35 will be opened. As the slide valve 38 opens, the liquid in the cylinder 20 will be forced out of arm 39 toward the pulse generating cylinder 56. As the cord 46 rewinds on the spring cylinder 50, the pulse generating cylinder 56 and the spring cylinder 50 will rotate in tandem. As the pulse generating cylinder 56 rotates, the central tubular path 58 will be alternatively blocked or unblocked. When it is unblocked, fluid will flow from arm 39 through the tubular path 58 and out of the output nozzle 40. When it is blocked no fluid will flow therethrough. Thus, the result will be a pulsating flow through the output nozzle 64 as the cylinder 56 rotates. The user would then repeat this process as many times as desired. The user can interrupt the flow of pulsating liquid by releasing the trigger at any time.

Those of ordinary skill in the art will recognize that many obvious modifications may be made thereto without departing from the spirit or scope of the present invention as set forth in the appended claims.

What is claimed is:

1. A manually powered pulsating liquid jet device for generating a pulsating flow for use in cleaning dentures comprising:
   a) a refillable liquid reservoir for holding liquid comprising a first inlet port through which the liquid enters the reservoir and a first outlet port;
   b) a one-way flow controller comprising a second inlet port and a second outlet port whereby the second inlet port is connected to the first outlet port to allow the liquid to exit but not to re-enter the reservoir therethrough;
   c) a piston with a handle external to the device and a mating cylinder connected to the second outlet port whereby withdrawing the piston from the cylinder will activate the one-way flow controller and cause liquid to be withdrawn from the reservoir;
   d) a spring loaded cord attached to the handle for pressurizing the liquid that is withdrawn from the reservoir;
   e) an outlet tube for the pressurized liquid comprising a first connection and a second connection whereby the first connection is fluidly connected to the second outlet port;
   f) a valve that can be moved from a first position to a second position for controlling flow of the pressurized liquid through the outlet tube;
   g) a rotating cylinder connected to the spring loaded cord comprising one or more central flow passages and a periphery with the openings on the ends of the central flow passages in the periphery adjacent to the second connection of the outlet tube; and
   h) an output nozzle adjacent to the rotating cylinder;
whereby moving the valve from the first position to the second position allows the pressurized liquid to flow through the second connection of the outlet valve, into, and through the one or more central flow passages and out of the output nozzle on a pulsating basis.

* * * * *